(12) United States Patent
Furuta (10) Patent No.: US 9,398,842 B2
(45) Date of Patent: Jul. 26, 2016

(54) ENDOSCOPE VALVE FOR CONTROLLING FLUID

(71) Applicant: HOYA CORPORATION, Tokyo (JP)

(72) Inventor: Tsuyoshi Furuta, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 97 days.

(21) Appl. No.: 14/368,630

(22) PCT Filed: Nov. 7, 2012

(86) PCT No.: PCT/JP2012/078863
§ 371 (c)(1),
(2) Date: Jun. 25, 2014

(87) PCT Pub. No.: WO2013/099445
PCT Pub. Date: Jul. 4, 2013

(65) Prior Publication Data
US 2015/0014567 A1 Jan. 15, 2015

(30) Foreign Application Priority Data
Dec. 26, 2011 (JP) .................. 2011-284128

(51) Int. Cl.
*A61B 1/00* (2006.01)
*A61B 1/015* (2006.01)
*A61B 1/005* (2006.01)

(52) U.S. Cl.
CPC .............. *A61B 1/015* (2013.01); *A61B 1/00068* (2013.01); *A61B 1/0052* (2013.01)

(58) Field of Classification Search
CPC ... A61B 1/00068; A61B 1/015; A61B 1/0052
USPC ................................. 251/318–324
See application file for complete search history.

(56) References Cited

U.S. PATENT DOCUMENTS 2,865,664 A * 12/1958 Robb .............. F16K 31/60
                                                                 192/69.63
3,958,566 A *  5/1976 Furihata ......... A61B 1/00068
                                                                 137/605

(Continued)

FOREIGN PATENT DOCUMENTS

EP     2095757      9/2009
JP     05-095897    4/1993

(Continued)

OTHER PUBLICATIONS

Search report from E.P.O., mail date is Apr. 13, 2015.

(Continued)

*Primary Examiner* — Kevin Murphy
*Assistant Examiner* — David Colon Morales
(74) *Attorney, Agent, or Firm* — Greenblum & Bernstein P.L.C.

(57) ABSTRACT

According to the present invention, an endoscope valve is provided that comprises a cylinder, a cylinder liner, a piston, and a sleeve. The cylinder has a groove on a lateral surface of the cylinder. The cylinder liner has a cylindrical shape and is inserted into an inner circumference of the cylinder. The piston is inserted into an inner circumference of the cylinder liner. The sleeve has a sleeve rib, a sleeve skirt, and a pin. The sleeve rib covers at least part of an open end of the cylinder. The sleeve skirt covers at least part of a circumferential surface of the open end. The pin projects from the sleeve skirt towards the circumferential surface to engage with the groove. The cylinder liner has a rib that projects radially outward from a circumference of the cylinder liner. The sleeve rib holds the rib on the open end in the case that the pin engages with the groove.

14 Claims, 12 Drawing Sheets

(56) References Cited

U.S. PATENT DOCUMENTS

| | | | | |
|---|---|---|---|---|
| 4,413,804 | A | * | 11/1983 | Lanius ............... F02M 37/0023 251/144 |
| 4,537,182 | A | * | 8/1985 | Otani ...................... A61B 1/12 251/325 |
| 4,800,869 | A | | 1/1989 | Nakajima |
| 4,860,731 | A | * | 8/1989 | Matsuura ........... A61B 1/00068 600/104 |
| 5,027,791 | A | * | 7/1991 | Takahashi .......... A61B 1/00068 600/158 |
| 5,257,773 | A | * | 11/1993 | Yoshimoto ............... A61B 1/12 251/339 |
| 5,322,263 | A | | 6/1994 | Yoshimoto et al. |
| 5,343,854 | A | * | 9/1994 | Katsurada ......... A61B 1/00068 600/146 |
| 5,433,410 | A | * | 7/1995 | Foltz ................. F01M 11/0408 251/100 |
| 5,466,020 | A | * | 11/1995 | Page ..................... F16L 37/252 215/332 |
| 5,840,015 | A | * | 11/1998 | Ogino ................ A61B 1/00068 600/153 |
| 5,840,016 | A | * | 11/1998 | Kitano .................... A61B 1/12 251/335.2 |
| 5,853,071 | A | * | 12/1998 | Robinson ............... B60T 11/30 188/352 |
| 5,871,441 | A | * | 2/1999 | Ishiguro ................. A61B 1/122 600/133 |
| 6,334,844 | B1 | * | 1/2002 | Akiba ...................... A61B 1/12 600/156 |
| 6,849,043 | B2 | * | 2/2005 | Kondo .................... A61B 1/12 600/159 |
| 6,908,429 | B2 | * | 6/2005 | Heimberger ....... A61B 1/00068 600/159 |
| 2009/0216084 | A1 | | 8/2009 | Yamane |
| 2009/0224196 | A1 | * | 9/2009 | Tanner ............... F16K 17/0493 251/321 |
| 2010/0049001 | A1 | * | 2/2010 | Yamane ................. A61B 1/015 600/159 |

FOREIGN PATENT DOCUMENTS

| | | |
|---|---|---|
| JP | 06-319699 | 11/1994 |
| JP | 07-039512 | 2/1995 |
| JP | 2009-201563 | 9/2009 |
| JP | 2009-201845 | 9/2009 |

OTHER PUBLICATIONS

Search Report from P.C.T., mail date is Dec. 4, 2012.
Office Action issued in China Counterpart Patent Appl. No. 201280064612.6, dated Nov. 30, 2015, along with an English translation thereof.

* cited by examiner

ENDOSCOPE VALVE FOR CONTROLLING FLUID

BACKGROUND OF THE INVENTION

1. Field of the Invention

The invention relates to a valve provided in an endoscope that controls a flow of fluid.

2. Description of the Related Art

An endoscope comprises a fluid supply line that carries fluid to a distal end of the endoscope and an inhalation line that carries various matter from the distal end. An endoscope valve is provided in the fluid supply line and the inhalation line, and controls the flow of fluid.

The endoscope valve mainly comprises a cylinder and a piston that is inserted into the cylinder. The cylinder and piston can be disassembled for maintenance or to be sterilized. A construction that installs the piston into the cylinder is disclosed in Japanese Publication of Unexamined Patent Application (HEI)5-95897 and Japanese Publication of Unexamined Patent Application 2009-201845. Japanese Publication of Unexamined Patent Application (HEI)5-95897 discloses a construction that engages a projection provided on a circumferential surface of the piston with a groove provided on an inner circumferential surface of a cylinder. Japanese Publication of Unexamined Patent Application 2009-201845 discloses a construction that inserts a projection provided on a circumferential surface of the piston into a guide groove provided completely around an inner circumference of a cylinder. The piston comprises a deformable plastic member. The projection and its circumference deform so that the projection moves into the groove in the cylinder. A construction that detaches the piston from the cylinder is disclosed in Japanese Publication of Unexamined Patent Application (HEI)5-95897. It discloses a construction in which a cam provided in the piston moves along a cam groove provided in the cylinder, so that the piston moves in the direction to which the piston comes off the cylinder.

SUMMARY OF THE INVENTION

An object of the present invention is to provide an endoscope valve in which a piston does not easily separate from the cylinder and which is easily assembled and disassembled.

According to the present invention, an endoscope valve that comprises a cylinder, a cylinder liner, a piston, and a sleeve is provided. The cylinder has a groove on a lateral surface of the cylinder. The cylinder liner has a cylindrical shape and is inserted into an inner circumference of the cylinder. The piston is inserted into an inner circumference of the cylinder liner. The sleeve has a sleeve rib, a sleeve skirt, and a pin. The sleeve rib covers at least part of an open end of the cylinder. The sleeve skirt covers at least part of a circumferential surface of the open end. The pin projects from the sleeve skirt towards the circumferential surface to engage with the groove. The cylinder liner has a rib that projects radially in an outer direction from a circumference of the cylinder liner. The sleeve rib holds the rib on the open end when the pin engages the groove.

BRIEF DESCRIPTION OF THE DRAWINGS

The objects and advantages of the present invention will be better understood from the following description, with reference to the accompanying drawings in which.

DESCRIPTION OF THE PREFERRED EMBODIMENTS

The present invention is described below with reference to the embodiments shown in the drawings. The first embodiment of the instant invention is shown in FIGS. 1-7.

Figure 1:
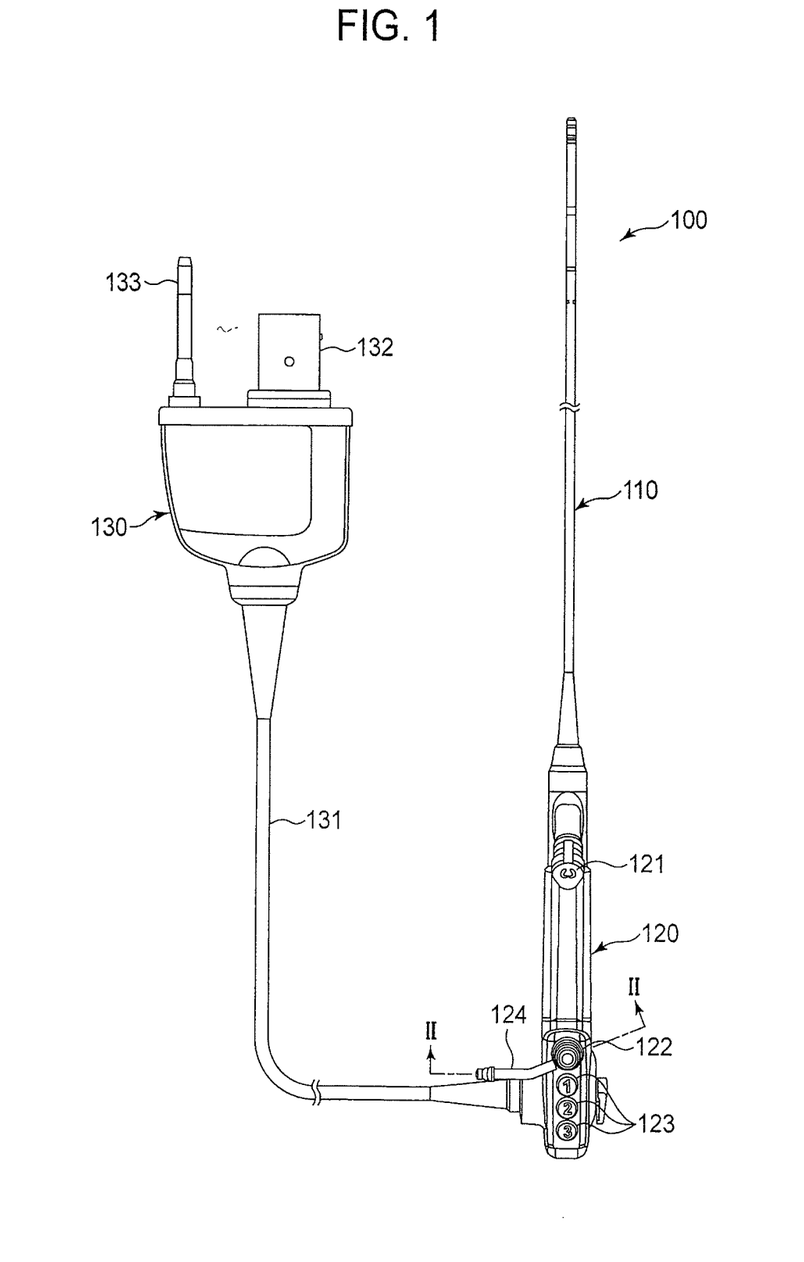
FIG. 1 is a schematic diagram showing an endoscope according to a first embodiment.

An endoscope 100 is described with reference to FIG. 1. The endoscope 100 mainly comprises an insertion member 110 that is inserted into the body of a subject, a control section 120 that is held by an operator, and a connector 130 that connects the endoscope 100 and a processor (not shown). A universal cable 131 connects the connector 130 and the control section 120.

A CCD unit (not shown), a vacuum opening, an illumination lens, etc., are provided in a distal end of the insertion member 110. A signal wire (not shown) is connected to the CCD unit. The CCD unit captures a subject image and sends it as an image signal through the signal wire to the connector 130. A vacuum tube (not shown) is connected to the vacuum opening. The vacuum opening extends along an inside of the insertion member 110 to the control section 120. The illumination lens is connected to an illumination fiber that extends from the connector 130 and emits illumination light toward a subject.

The control section 120 comprises a forceps opening 121, a first endoscope valve 122, and a switch 123. The forceps opening 121 is connected to the vacuum tube. Forceps inserted into the forceps opening 121 are carried to the distal end through the inside of the vacuum tube. The first valve 122 is connected to a negative pressure nipple 124, and supplies negative pressure to the vacuum opening when the first valve 122 is depressed. A negative pressure tube (not shown) is connected to the negative pressure nipple 124 and supplies negative pressure to the first valve 122. In the case that the first valve 122 is depressed, the negative pressure nipple 124 is connected to the vacuum opening, so that negative pressure is supplied to the vacuum opening. The valve 122 is described in greater detail later. The switch 123 is used to operate the endoscope 100 and the processor.

The connector 130 has a signal terminal 132 that is connected to the processor (not shown) and an illumination terminal 133 that is connected to an illumination unit (not shown). The signal terminal 132 is connected to a signal wire in the connector 130 and sends image signals from the CCD unit to the processor. The illumination terminal 133 is connected to an illumination fiber in the connector 130 and carries illumination light to the illumination lens.

Figure 2:
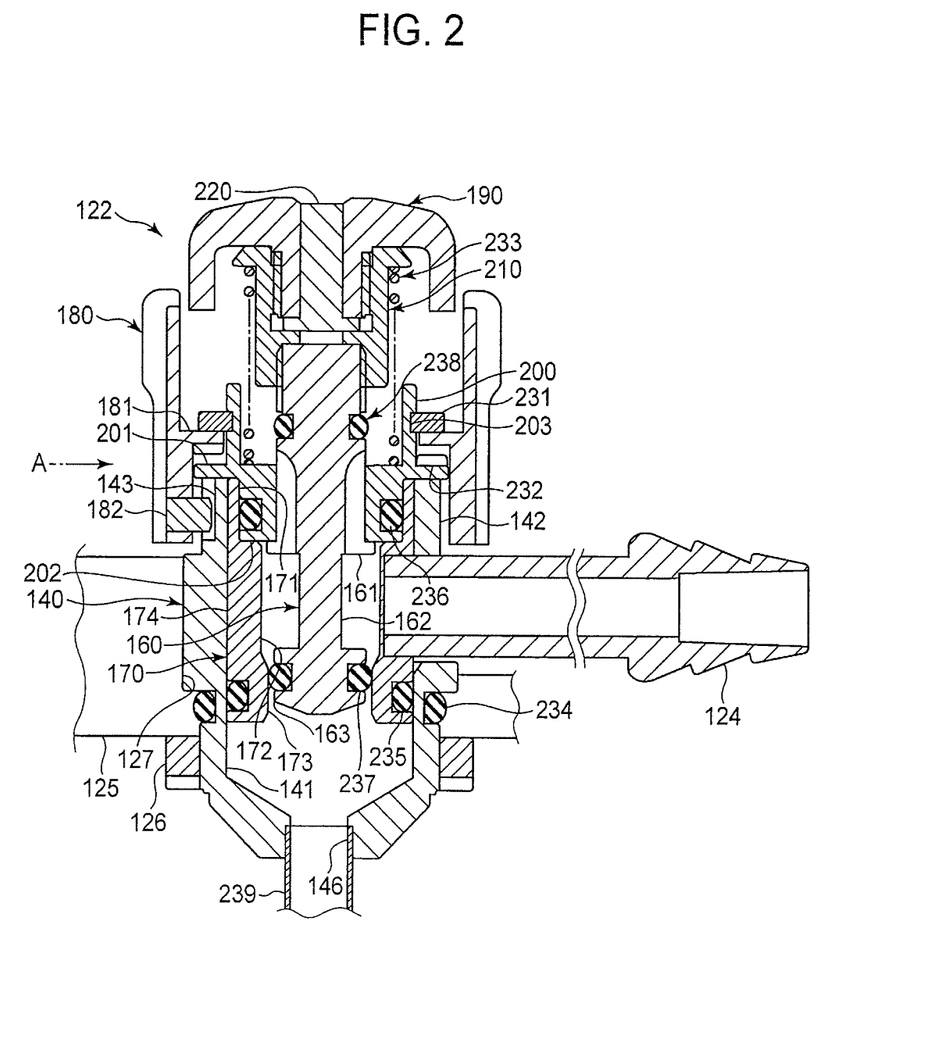
FIG. 2 is a cross sectional view of the endoscope valve at the II-II line of FIG. 1.

The detail of the valve 122 is described with reference to FIG. 2. The first valve 122 mainly comprises a cylinder 140, a piston 160, a first cylinder liner 170, a first sleeve 180, and a negative pressure nipple 124.

The cylinder 140 is closed at the bottom and comprises a cylinder inner surface 141 that is a cylinder, a slit 143 that is provided in a cylindrical outer circumferential surface 142, and a negative pressure hole 146 that opens at the bottom. The cylinder 140 is inserted into a valve hole 127 from an exterior of the control section 120, and fixed by a stopper tube 126 configured on an inner surface of an external wall of the control section 120. The valve hole 127 opens into the external wall of the control section 120. A first O-ring 234 is provided between the cylinder outer circumferential surface 142 and the valve hole 127, and maintains an airtight seal between the inside and outside of the control section 120. The negative pressure hole 146 is connected to an inhalation line 239 that extends from the vacuum opening.

The piston 160 is cylindrical. The first cylinder liner 170 is cylindrical and has an engagement part 171, a fluid channel 172, and an outflow channel 173, and is inserted into the circumferential surface of the cylinder 140 so that an outer circumferential surface 174 makes contact with the cylinder inner surface 141. As for the dimensions in the radial direction of the first cylinder liner 170, the length of the engagement part 171 is thinnest, the fluid channel 172 is wider than the engagement part 171, and the outflow channel 173 is the widest of the three.

The piston 160 has a piston rib 161 that projects from substantially the center of the axis of the piston 160 radially outwards around the whole circumference of the piston 160, a small diameter section 162 that is relatively narrow in the radial direction, and a tip 163 that has a larger diameter than the small diameter section 162. One third of the full length of the piston 160 is inserted into the inner circumference of the first cylinder liner 170. A tubular seat 200 is inserted between the inner circumference of the first cylinder liner 170 and the piston 160. The first cylinder liner 170 and the seat 200 form a cylindrical cylinder liner that is inserted in the inner circumferential surface 141 of the cylinder 140. A fourth O-ring 237 is configured around the circumference of the tip 163. A fifth O-ring 238 is configured around the piston above the small diameter section 162 on the other end from the tip 163.

The seat 200 has a ring groove 203 that is provided on the outer circumferential surface 174 and a first receiver rib 201 that projects from substantially the center of the axis of the seat 200 radially outwards around the whole circumference of the seat 200. Substantially one half to the full length of the seat 200 is inserted into the inner circumference of the engagement part 171. The first receiver rib 201 engages with the end of the first cylinder liner 170 and the end of the cylinder 140. An end surface 202 of the seat 200 engages with the piston rib 161.

The first sleeve 180 is cylindrical and covers the outer circumference of the seat 200 and a part of the outer circumference of the cylinder 140. The sleeve 180 has a sleeve rib 181 that projects from substantially the center of the axis of the sleeve 180 radially inwards around the whole circumference of the sleeve 180 and a dowel 182 that is provided near an end of the inner circumferential surface of the sleeve 180. After the seat 200 and the cylinder 140 is inserted into the sleeve 180 for substantially one half of the axial length of the seat 200, the dowel 182 engages with the slit 143 in the case that the sleeve 180 is rotated in a circumferential direction, so that the sleeve 180 is fixed to the cylinder 140 in the axial and circumferential direction.

A wave washer 232 is provided between the sleeve rib 181 and the first receiver rib 201, and biases the sleeve 180 in the direction where the first sleeve 180 separates from the seat 200 and the cylinder 140. A C-clip 231 is provided on a back of a surface where the wave washer 232 is provided. The C-clip 231 is an external snap ring, and composes a holder. An inner circumferential surface of the C-clip 231 engages with the ring groove 203, so that the C-clip 231 is fixed in the axial direction and is rotatable in the circumferential direction. An end surface 202 of the C-clip 231 engages the sleeve rib 181. Therefore, the sleeve 180 is fixed to the seat 200 in the axial direction.

The sleeve 180 is fixed to the cylinder 140 in the axial and circumferential directions by the dowel 182, and fixed to the seat 200 in the axial direction by the C-clip 231. Thereby, the seat 200 is fixed to the first cylinder liner 170 and the cylinder 140. The piston rib 161 of the piston 160 engages with an end surface 202 of the seat 200. Thereby, the piston 160 is fixed to the cylinder 140 and the first cylinder liner but movable in the axial direction with respect to the first cylinder liner 170. The first cylinder liner 170 is fixed in the axial direction and rotatably fixed by the seat 200.

A second O-ring 235 is provided between the outer circumferential surface 174 of the first cylinder liner 170 and the inner circumferential surface of the cylinder 140, and maintains an airtight seal between the outer circumferential surface 174 and the inner circumferential surface of the cylinder 140. A third O-ring 236 is provided between the outer circumferential surface of the first cylinder liner 170 and the inner circumferential surface of the seat 200, and maintains an airtight seal between the outer circumferential surface of the seat 200 and the inner circumferential surface of the cylinder 140.

The negative pressure nipple 124 is inserted into a hole that penetrates a lateral surface of the cylinder 140 and the first cylinder liner 170, and penetrates into an inner circumferential surface of the fluid channel 172. Thereby, negative pressure that flows into the negative pressure nipple 124 is provided to an inner circumferential surface of the first cylinder liner 170.

A push button 190 is provided on an end of the piston 160. The push button 190 is exposed to an outer surface of the valve 122 so that a user can push the push button. A compression coil spring 233 is provided between the push button 190 and the first receiver rib 201, and biases the push button 190 and the piston 160 in the displacement direction of the piston 160 from the first cylinder liner 170. An indicator 220 is provided at the center of the push button 190. The indicator 220 is a sign that allows a user to recognize that it is the valve 122.

The construction of the valve 122 where the push button 190 is not depressed is described with reference to FIG. 2.

The push button 190 is biased toward the upper direction along the axis of the valve 122 by the compression coil spring 233 when a user does not push the push button 190. Thereby, the piston connected to the push button 190 is kept in an upper position along the axis of the valve 122. At this moment, a tip 163 of the piston 160 is close to an outflow channel 173 of the first cylinder liner 170, and the fourth O-ring 237 is provided between the tip 163 and the outflow channel 173, so as to maintain an airtight seal between the tip 163 and the outflow channel 173. Thereby, the negative pressure nipple 124 is not connected to the inhalation line 239, so that negative pressure that flows into the inside of the first cylinder liner 170 from the negative pressure nipple 124 does not flow into the inhalation line 239.

Figure 3:
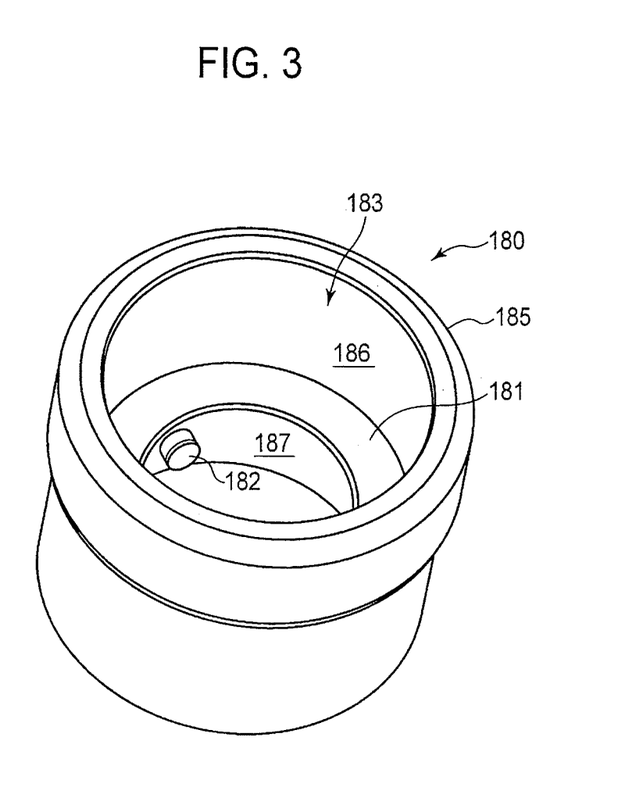
FIG. 3 is a perspective view of a first sleeve obliquely from above.
Figure 4:
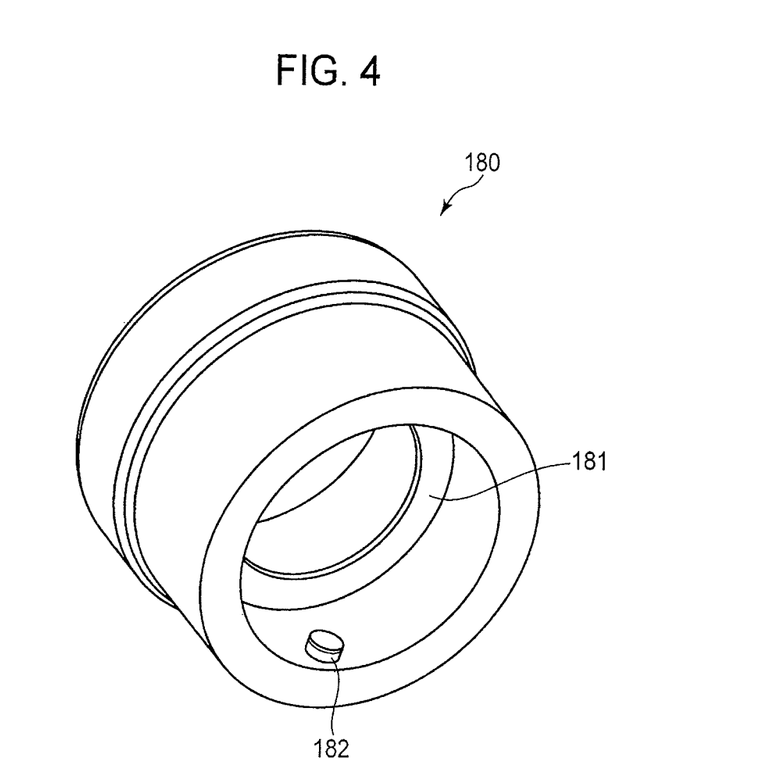
FIG. 4 is a perspective view of the first sleeve obliquely from below.

The first sleeve 180 is described below with reference to FIGS. 3 and 4.

The first sleeve 180 comprises a sleeve body 183 of metal, a lining 185 that covers the outer circumferential surface 174 of the sleeve body 183, and a dowel 182 that projects from the inner circumferential surface of the sleeve body 183.

The sleeve body 183 is substantially cylindrically shaped. The sleeve rib 181 projects radially inward around the whole circumference at approximately the midpoint along the axial direction of the cylindrically shaped sleeve body 183. The dowel 182 is configured on the inner circumferential surface near and end of the sleeve 180 along the axial direction. The sleeve body 183 has a sleeve upper end 186 located above the sleeve rib 181 where the dowel 182 is not provided, and a sleeve skirt 187 located below the sleeve rib 181 where the dowel 182 is provided. The sleeve rib 181 projects from the sleeve skirt 187. The thickness in the radial direction of the sleeve upper end 186 is thinner than that of the sleeve skirt 187.

The dowel 182 has a cylindrical shape. The preferable length along the axial direction of the dowel 182 is two times to the thickness of the sleeve skirt 187 in the radial direction, but it is not limited to that length. The dowel 812 fits into the hole that penetrates from the outer circumferential surface to the inner circumferential surface of the sleeve skirt 187, so that the dowel 182 is fixed to the sleeve body 183.

The lining 185 comprises an elastic body. The thickness of the lining 185 along the side of the sleeve upper end 186 is greater than that on the side of the sleeve skirt 187.

Figure 5:
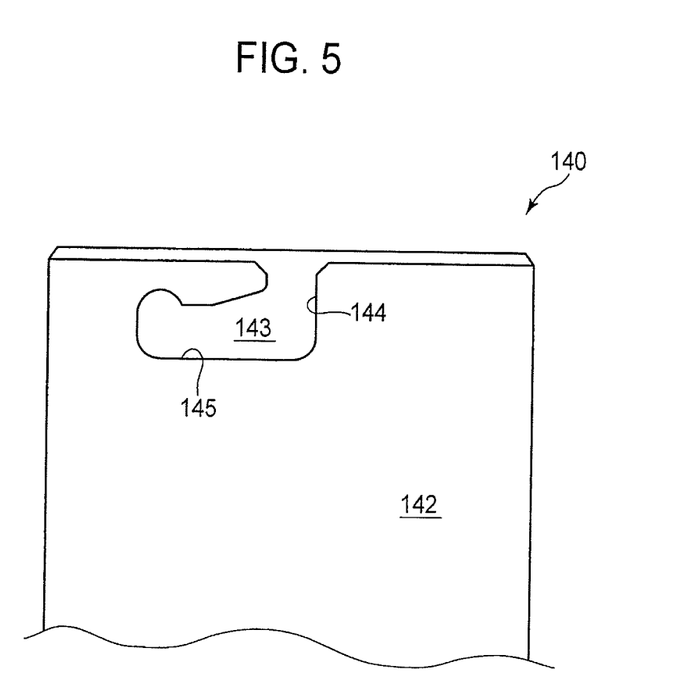
FIG. 5 is a side view of a cylinder along the A-direction of FIG. 2.

The slit 143 is described below with reference to FIG. 5.

The slit 143 is a groove that is provided on the outer circumferential surface 142 of the cylinder 140. From an exterior perspective along its radial direction, the cylinder 140 has groove 144 with an overturned L shape that slightly extends from the top of the cylinder 140 along its axis, and groove 145 in the circumferential direction that extends along the circumference of the cylinder 140.

The width of groove 144 in the axial direction, i.e. the length along its circumference, is longest at the top of the cylinder 140, and becomes narrower with increasing distance from the top of the cylinder in the axial direction. Then, at the place where the width of groove 144 is a certain length, the axial direction groove 144 extends along the axis with the certain length.

The circumference direction groove 145 extends orthogonally in the circumferential direction from the end of the axial direction groove 144. The width of the circumferential direction groove 145, i.e. the length in the axial direction of the cylinder, is longest at the connection point with the axial direction groove 144, and becomes narrower as it extends in the circumferential direction. At the place where the width of circumference direction groove 145 is a certain length, the circumferential direction groove 145 extends along the circumferential direction at the certain length. The width of the end of the groove is wider than the certain length.

Figure 6:
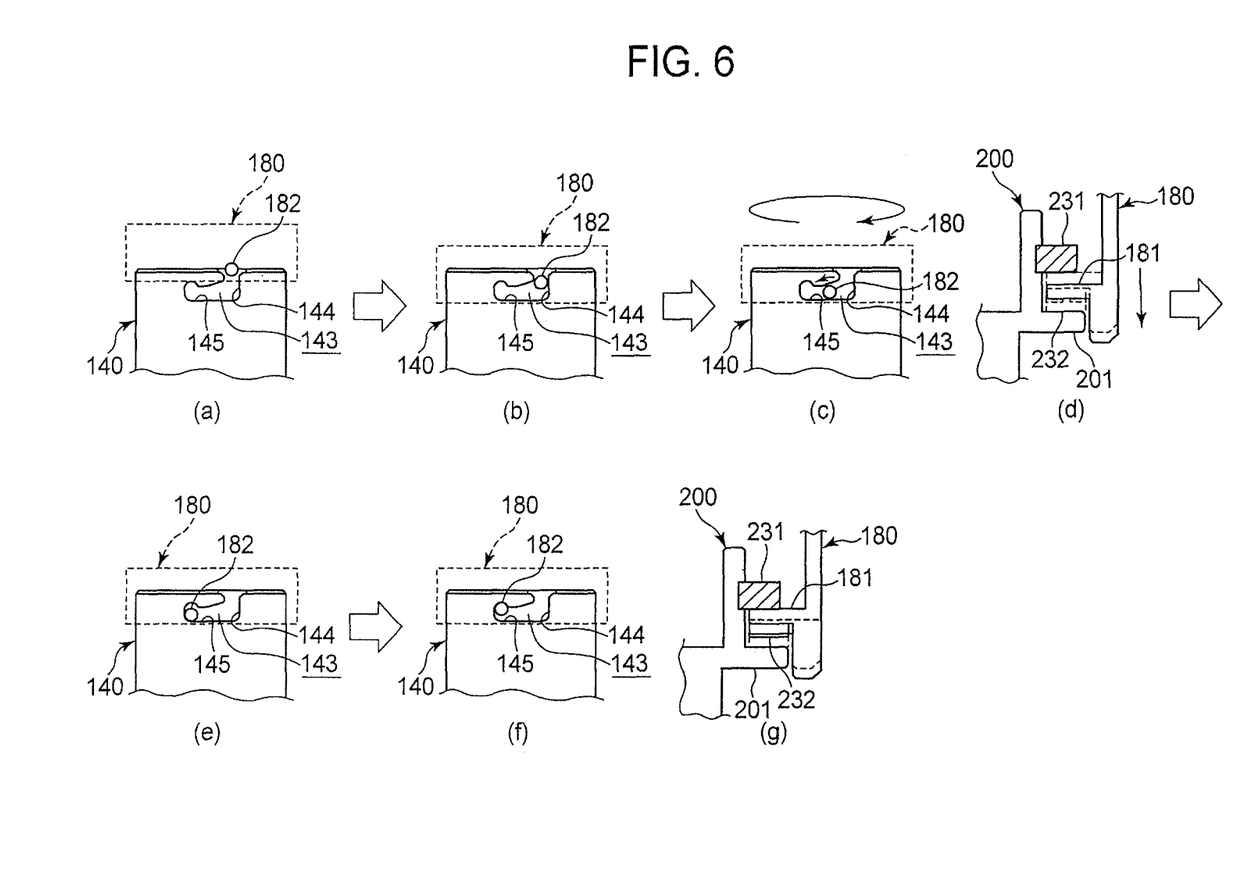
FIG. 6 shows a process for installing a piston into the cylinder.

The process that fixes the first sleeve 180 to the cylinder 140 is described below with reference to FIG. 6.

FIG. 6(a) shows the first sleeve 180 and the cylinder 140. The first sleeve 180 is placed on the top of the cylinder 140 after the dowel 182 is aligned with the axial direction groove 144. The dowel 182 is easily aligned with the axial direction groove 144 because the width of the axial direction groove 144 widens at the top of the cylinder 140. A user pushes the first sleeve 180 into the cylinder 140 after aligning the dowel 182 with the axial direction groove 144. Then, the dowel 182 moves into the axial direction groove 144.

FIG. 6(b) shows the first sleeve 180 that is pushed into the cylinder 140. The dowel 182 is located at approximately the center of the axial direction groove 144. The dowel 182 moves downward along the axial direction groove 144.

FIG. 6(c) shows the first sleeve 180 that is rotated against the cylinder 140 by a user. The dowel 182 moves toward the circumferential direction groove 145 from the axial direction groove 144 when a user rotates the first sleeve 180 against the cylinder 140. The dowel 182 easily moves into the circumferential direction groove 145 from the axial direction groove 144 because the width of the circumferential direction groove 145 is wider at the connection point with the axial direction groove 144. The dowel 182 moves in the axial and circumferential direction along an upper wall of the circumferential direction groove 145 after it penetrates into the circumferential direction groove 145. A user needs to push the first sleeve 180 into the cylinder 140 with a certain force because a wave washer 232 biases the first sleeve 180 upward along the axis. However, a user can easily move the dowel 182 in the axial direction because the dowel 182 moves along the upper wall of the circumferential direction groove 145.

FIG. 6(d) shows the first sleeve 180, the seat 200, and the wave washer 232 at the same moment as FIG. 6(c). As described hereinbefore, the dowel 182 moves in the axial direction along the upper wall of the circumferential direction groove 145 when a user rotates the first sleeve 180 against the cylinder 140. At this time, the sleeve rib 181 deforms the wave washer 232, which is positioned between the sleeve rib 181 and the first receiver 201 in the axial direction, and moves toward the first receiver rib 201.

FIG. 6(e) shows the first sleeve 180 and the cylinder 140 where a user finishes rotating the first sleeve 180 against the cylinder 140. The dowel 182 touches the end of the circumferential direction groove 145.

FIG. 6(f) shows the first sleeve 180 that is finally attached to the cylinder 140. The dowel 182 is located at the upper end of the circumferential direction groove 145. After a user finishes rotating the first sleeve 180 against the cylinder 140 and let's go of the first sleeve 180, the dowel 182 moves upward in the axial direction because the first sleeve 180 is biased upward in the axial direction. The dowel 182 engages the upper end of the circumferential direction groove 145 and cannot move in the circumferential direction because the end of the circumferential direction groove 145 is relatively wider than the rest of the groove.

FIG. 6(g) shows the first sleeve 180, the seat 200, and the wave washer 232 at the same moment as FIG. 6(f). At that moment, the sleeve rib 181 moves upward and its position is higher than that shown in FIG. 6(d).

Figure 7:
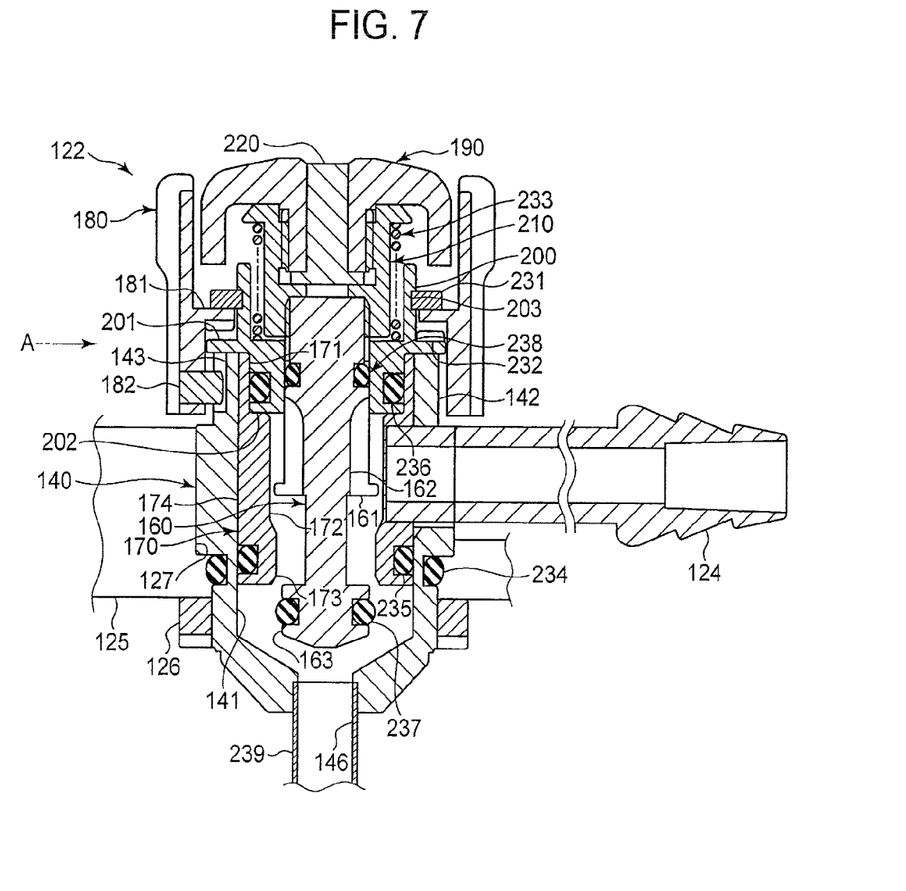
FIG. 7 is a cross sectional view showing the piston being pushed into the cylinder.

The construction of the valve 122 where the push button 190 is fully pushed down is described with reference to FIG. 7.

A user pushes the push button 190, so that the piston 160 that is connected to the push button 190 is pushed downward in the axial direction. In the case that the top of the push button 190 is pressed into the top of the first sleeve 180, the small diameter section 162 of the piston 160 moves down in the axial direction beyond the outflow channel 173 of the first cylinder liner 170. Thereby, the negative pressure nipple 124 is connected to the inhalation line 239, so that negative pressure flows into the inside of the first cylinder liner 170 from the negative pressure nipple 124, and flows into the inhalation line 239. A fifth O-ring 238 is caught between the piston 160 and the inner circumferential surface of the seat 200, and maintains an airtight seal between the seat 200 and the piston 160. Thereby, the insides of the inhalation line 239, the negative pressure nipple 124, and the first cylinder liner 170 are not exposed to the atmosphere, so that negative pressure that flows into the insides of the inhalation line 239, the negative pressure nipple 124, and the first cylinder liner 170 does not flow outside of the first valve 122. Therefore, matter that is inhaled from the distal end of the endoscope 100 and carried to the first valve 122 through the inhalation line 239 does not leak out of the first valve 122.

According to the instant embodiment, the first sleeve 180 and the cylinder 140 are made of metal, so that wear by mounting or dismounting is minimized, thus extending the life of the first valve 122.

The first cylinder liner 170 is rotatable with respect to the cylinder 140, so that a load applied by the negative pressure tube to the negative pressure nipple 124 is minimized even if the control section 120 is moved in the case that the negative pressure tube is connected to the negative pressure nipple 124.

The first sleeve 180 and the cylinder 140 are isolated in the rotating direction from the first cylinder liner 170, which is connected to the negative pressure nipple 124, so that a load from the negative pressure tube is not applied to the first sleeve 180 or the cylinder 140, and dislodging the first sleeve 180 is difficult even if the control section 120 is moved when the negative pressure tube is connected to the negative pressure nipple 124.

The first valve 122 can be assembled and disassembled only by rotating the first sleeve 180, which ensures that it is properly assembled and disassembled and the number of parts is reduced.

Figure 8:
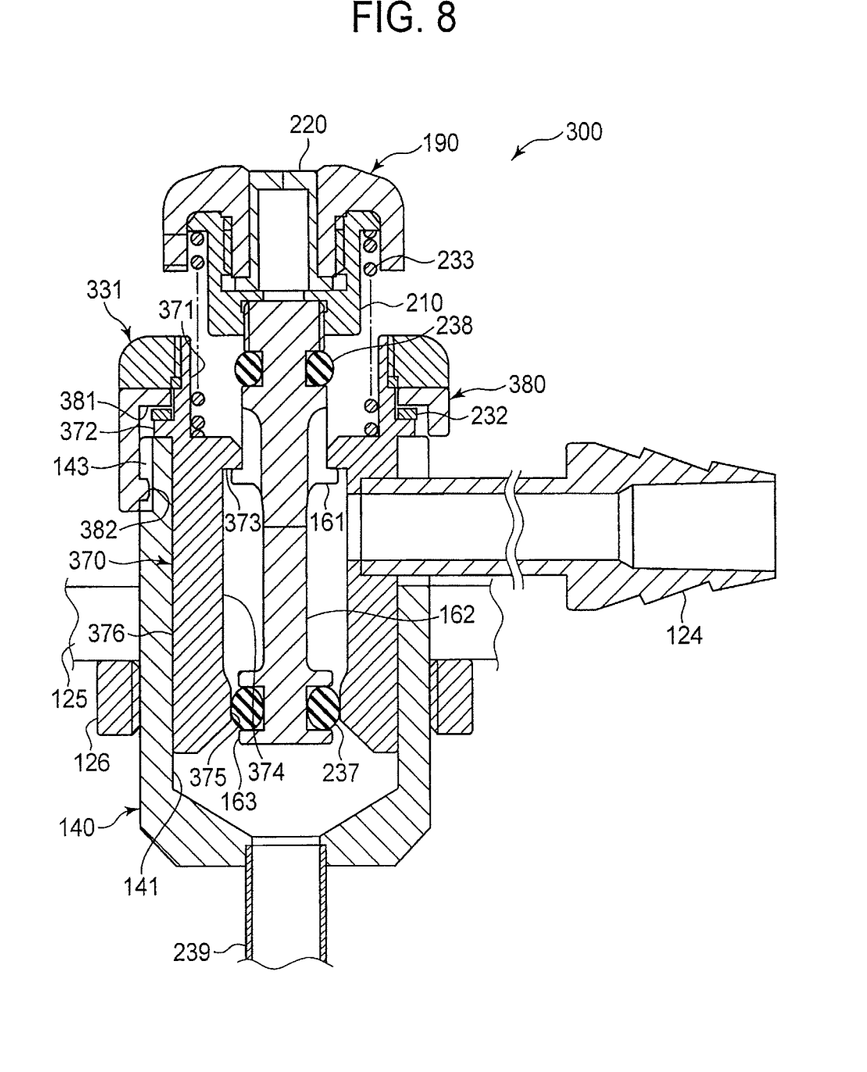
FIG. 8 is a cross sectional view of a valve of an endoscope according to a second embodiment.
Figure 9:
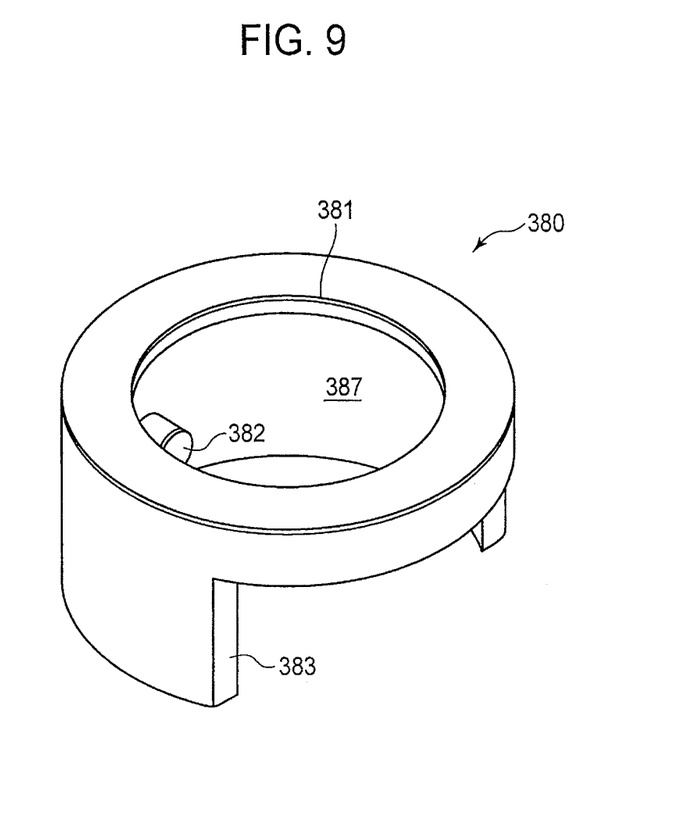
FIG. 9 is a perspective view of a second sleeve obliquely from above.
Figure 10:
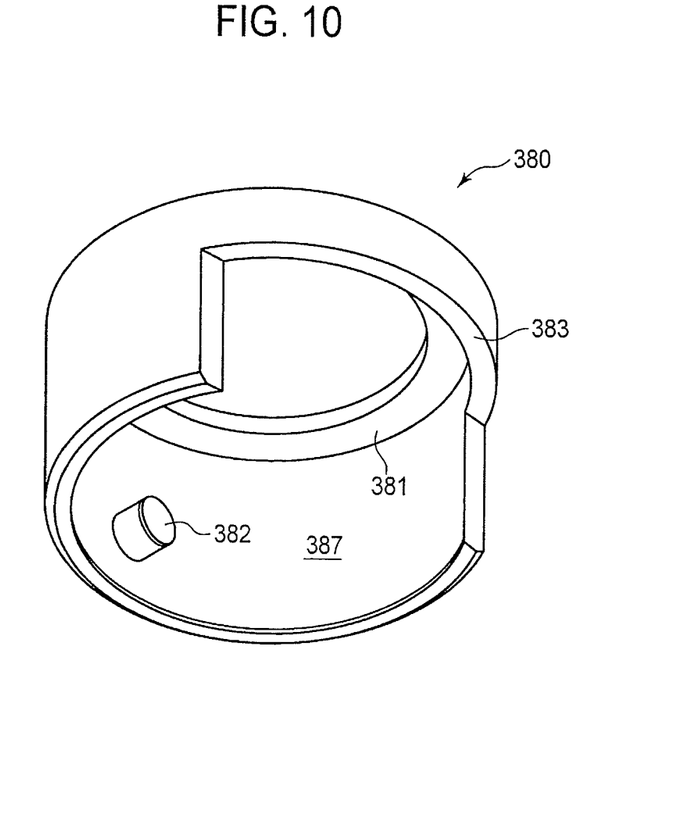
FIG. 10 is a perspective view of the second sleeve obliquely from below.

The second valve 300 of the second embodiment is described with reference to FIGS. 8-10. The constructions of the second embodiment that are similar to the first embodiment have the same numerical figures applied and their descriptions have been omitted.

The detail of the second valve 300 is described with reference to FIG. 8.

The second valve 300 mainly comprises a cylinder 140, a piston 160, a second cylinder liner 370, a second sleeve 380, and a negative pressure nipple 124. The second cylinder liner 370 is constructed as a cylindrical cylinder liner that is inserted in the inner circumferential surface 141 of the cylinder 140. The constructions of the piston 160 are similar to the first embodiment, so that their descriptions have been omitted.

The second cylinder liner 370 has a cylindrical shape and comprises a second engagement part 371, a second receiver rib 372, an inner rib 373, a second fluid channel 374, and a second outflow channel 375 in order from top to bottom along its axis. The second engagement part 371 that is provided on the top end of the second cylinder liner 370 is thickest in the radial direction. The second receiver rib 372 projects from an outer circumferential surface 174 of the second cylinder liner 370 radially outward around the entire circumference of the cylindrical shape. The inner rib 373 projects from an inner circumferential surface of the second cylinder liner 370 radially inward around the entire circumference of the cylindrical shape. The width of the second outflow channel 375 in the radial direction is narrower than that of the inner rib 373. The second fluid channel 374 is provided on the bottom end of the second cylinder liner 370, and projects from an inner circumferential surface of the second cylinder liner 370 radially inward around the entire circumference of the cylindrical shape. The width of the second fluid channel 374 in the radial direction is less than that of the inner rib 373 and the width of the second outflow channel 375 and is greater than that of the second engagement part 371. The second cylinder liner 170 is inserted into the inner circumferential surface of the cylinder 140 until the second receiver rib 372 engages with the end of the cylinder 140, that is, the part from the inner rib 373 to the second fluid channel 374 is inserted into the inner circumference of the cylinder 140, so that an outer circumferential surface 174 of the second cylinder liner 370 engages with the cylinder inner surface 141. That is, the second engagement part 371 and the second receiver rib 372 are not inserted into the inner circumference of the cylinder 140.

The second sleeve 380 is cylindrically shaped and covers a part of the outer circumference of the second cylinder liner 370 and the cylinder 140. The second sleeve 380 has a second sleeve rib 381, which projects radially inward around the entire circumference of the second sleeve 380 from its upper end in the axial direction, and a second dowel 382 that is provided near an end of the second inner circumferential surface 387 of the second sleeve 380.

After the second cylinder liner 370 and the cylinder 140 are inserted into the inner circumference of the second sleeve 380, the second dowel 382 engages with the slit 143 when the second sleeve 380 is rotated in a circumferential direction, so that the second sleeve 380 is fixed to the cylinder 140 in the axial and circumferential directions.

A wave washer 232 is provided between the second sleeve rib 381 and the second receiver rib 372, and biases the second sleeve 380 upwards in the axial direction to where the second sleeve 380 separates from the cylinder 140.

A ring 331 is provided on a back of a surface where the wave washer 232 is provided. A female screw is threaded into the inner circumferential surface of the ring 331. Then, a male screw that is formed on the outer circumferential surface 174 of the second engagement part 371 is screwed into the inner circumferential surface of the ring 331, so that the ring 331 is fixed in the axial direction. Thereby, the second engagement part 371 is push onto the end of the cylinder 140 with the wave washer 232 and the second cylinder liner 370 is fixed to the cylinder 140 in the axial direction.

The constructions of the second valve 300 when the push button 190 is depressed and when it is not depressed are similar to the first embodiment, so that their descriptions have been omitted.

The second sleeve 380 is described below with reference to FIGS. 9 and 10.

The second sleeve 380 is substantially cylindrical, and has the second sleeve rib 381, a cutout 383 that is provided on a side wall, and the second dowel 382 that projects from its inner circumferential surface.

The second sleeve rib 381 projects from the upper end of the second sleeve 380 radially inward around the entire circumference. The side wall of the second sleeve 380 has a 45 degree cut at an axial angle so that the cutout 383 is formed. Referring to FIG. 8, in the case that the second valve 300 is fully assembled, the negative pressure nipple 124 is positioned at the cutout 383 and can be rotated up to 45 degrees around the axis of the second sleeve 380. The second dowel 382 is provided on the inner circumferential surface near the end, in the axial direction, of the second sleeve 380. The second dowel 382 has a cylindrical shape. The preferable length along the axial direction of the second dowel 382 is one half to the thickness in the radial direction of the bottom of the second sleeve 380, but it is not limited to that length.

The process that fixes the second sleeve 380 to the cylinder 140 is similar to the first embodiment, so that their descriptions have been omitted.

According to the instant embodiment, the similar effects as the first embodiment are obtained, and relatively fewer parts are required compared to the first embodiment.

Please note that the cutout 383 need not be 45 degrees; another angle may be chosen.

Figure 11:
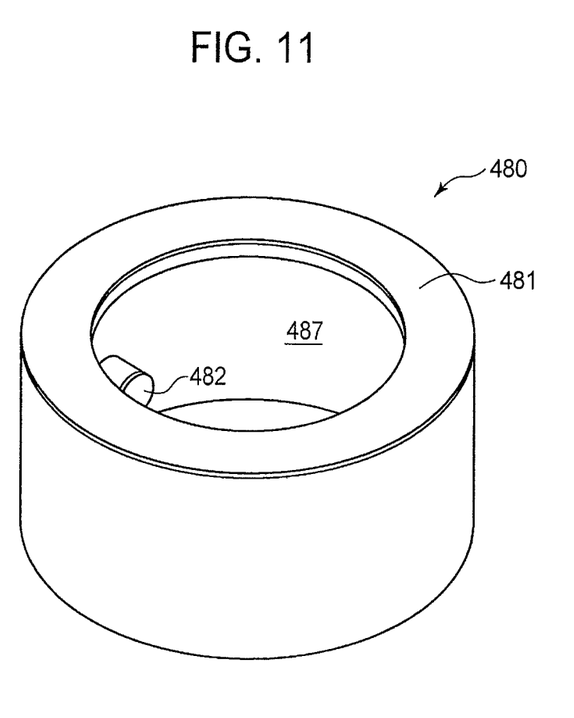
FIG. 11 is a perspective view of a third sleeve according to a third embodiment obliquely from above.
Figure 12:
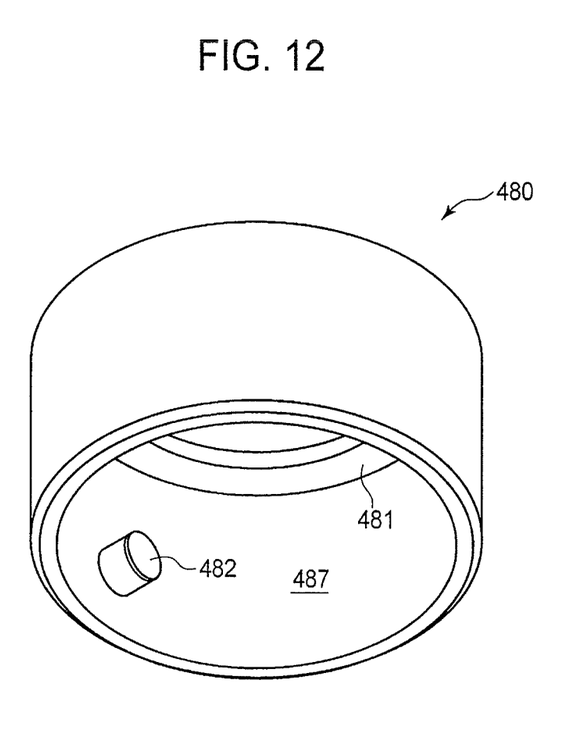
FIG. 12 is a perspective view of the third sleeve obliquely from below.

The third valve 400 of the third embodiment is described with reference to FIGS. 11 and 12. In the instant embodiment, the third sleeve 480 differs from the second sleeve 480. Therefore, the third sleeve 480 is mainly described hereinafter, and the constructions of the third embodiment that are similar to the first and second embodiments have the same numerical figures applied and their descriptions have been omitted.

The third sleeve 480 is substantially cylindrical and has a third sleeve rib 481, which projects radially inward around the entire circumference of the third sleeve 480 from its upper end in the axial direction, and a third dowel 482 that is provided near an end of the third inner circumferential surface 487. The cutout 383 of the second embodiment is not provided. The third dowel 482 has cylindrical shape. The preferable length along the axial direction of the third dowel 482 is one half to the thickness in the radial direction of the bottom of the third sleeve 480, but it is not limited to that length.

The process that fixes the third sleeve 480 to the cylinder 140 is similar to the first embodiment, so their descriptions have been omitted.

According to the instant embodiment, the similar effects as the first embodiment are obtained, and the number of parts required is relatively fewer than the first embodiment.

Please note that the first, second, and third sleeves 180, 380, and 480 and the cylinder 140 need not be made of metal, and may be made of another material that endures pressure and heating from sterilization and minimizes wear from connecting and disconnecting.

The wave washer 232 may be made of another elastic body.

The shape of the slit 143 need not be limited to that described hereinbefore. The circumferential direction groove 145 need not be orthogonal to the axis. It may have a shape that restricts movement of the first, second, and third sleeves 180, 380, and 480 in the upper axial direction.

The cylinder 140, the piston 160, the first and second cylinder liner 170 and 370, and the first, second, and third sleeves 180, 380, and 480 need not be cylindrical.

The angle of the cutout 383 need not be 45 degrees; another angle may be chosen.

Although forms of the invention have been described herein, it will be obvious to those skilled in the art that variations may be made in the construction and relation of parts without departing from the spirit and scope of the invention described herein.

The present disclosure relates to subject matter contained in Japanese Patent Application No. 2011-284128 (filed on Dec. 26, 2011), which is expressly incorporated herein, by reference, in its entirety.

The invention claimed is:

1. A endoscope valve comprising:
a cylinder that has a groove on a lateral surface of the cylinder;
a cylinder liner that has a cylindrical shape and is positioned within an inner circumferential surface of the cylinder;
a piston that is positioned within an inner circumferential surface of the cylinder liner;
a sleeve that has a sleeve rib, a sleeve skirt, and a pin, the sleeve rib covering at least part of an open end of the cylinder, the sleeve skirt covering at least part of a circumferential surface of the open end of the cylinder, and the pin projecting from the sleeve skirt towards the circumferential surface to engage with the groove;
the cylinder liner has a rib that projects from a circumferential surface of the cylinder liner radially in an outward direction
an elastic body provided between the sleeve rib and the rib, in an axial direction of the cylinder;
a holder provided on a lateral surface of the cylinder liner and engages the sleeve rib, the elastic body biases the sleeve rib in a direction that is opposite to the open end of the cylinder, so as to engage the sleeve rib with the holder; and
the sleeve rib holds the rib on the open end of the cylinder when the pin engages the groove.

2. The endoscope valve according to claim 1, wherein the cylinder liner is held rotatably on the cylinder.

3. The endoscope valve according to claim 1, wherein the groove extends orthogonally to an axis of the cylinder.

4. The endoscope valve according to claim 1, wherein the cylinder liner further comprises a seat that is attached to an opening of the cylinder liner, the piston comprises a piston rib that projects from a circumferential surface of the piston radially in an outward, the seat comprises a projection that projects from an inner circumferential surface of the cylinder liner radially inward, and the piston does not move beyond a certain position and is rotatable with respect to the cylinder liner when the piston rib engages with the projection.

5. The endoscope valve according to claim 1, wherein the piston comprises a piston rib that projects from a circumferential surface of the piston radially outward, the cylinder liner further comprises a projection that projects from an inner circumferential surface of the cylinder liner radially inward, and the piston does not move beyond a certain position and is rotatable with respect to the cylinder liner when the piston rib engages with the projection.

6. The endoscope valve according to claim 1, wherein the sleeve has a cylindrical shape, the cylindrical shape has a recess, and the sleeve skirt extends for a predetermined circumferential distance around an axis of the sleeve.

7. The endoscope valve according to claim 1, wherein the cylinder has a bottom, the sleeve skirt covers a predetermined portion of the piston in the circumferential direction, and the sleeve rib is a ring that covers the entire circumference of the open end.

8. The endoscope valve according to claim 1, wherein the elastic body is a ring washer.

9. The endoscope valve according to claim 1 wherein a first tube opening is provided in a bottom of the cylinder, and a second tube opening is provided in a lateral surface of the cylinder liner, and the first tube opening is connected to the second tube opening when the piston is inserted to a first position in the cylinder, and connection between the first tube opening and the second tube opening is closed when the piston is inserted to a second position in the cylinder, the second position is shallower than the first position.

10. The endoscope valve according to claim 1, wherein the elastic body comprises a wave washer.

11. The endoscope valve according to claim 1, wherein the holder comprises a C-clip.

12. The endoscope valve according to claim 1, wherein the groove comprises a L-shaped slit.

13. The endoscope valve according to claim 1, wherein the holder comprises a member discrete from the cylinder liner and from the sleeve.

14. The endoscope valve according to claim 13, wherein the holder is engageable with a surface of the sleeve rib.

* * * * *